(12) United States Patent
Matsumoto

(10) Patent No.: US 9,087,446 B2
(45) Date of Patent: Jul. 21, 2015

(54) LIFE MANAGEMENT APPARATUS AND LIFE MANAGEMENT METHOD

(71) Applicant: Mitsubishi Electric Corporation, Tokyo (JP)

(72) Inventor: Takashi Matsumoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 14/074,030

(22) Filed: Nov. 7, 2013

(65) Prior Publication Data

US 2014/0184414 A1    Jul. 3, 2014

(30) Foreign Application Priority Data

Dec. 28, 2012    (JP) ................................ 2012-288022

(51) Int. Cl.
  *G08B 23/00*    (2006.01)
  *G08B 21/06*    (2006.01)
  *G06F 19/00*    (2011.01)

(52) U.S. Cl.
  CPC ............ *G08B 21/06* (2013.01); *G06F 19/3481* (2013.01)

(58) Field of Classification Search
  CPC ......... A61B 5/18; A61B 5/6892; G08B 21/06
  USPC ........ 340/575, 576, 425.5, 691.1, 691.3, 692; 600/483, 500, 519, 595
  See application file for complete search history.

(56) References Cited

U.S. PATENT DOCUMENTS

| | | | |
|---|---|---|---|
| 8,098,165 B2* | 1/2012 | Demirdjian et al. .......... | 340/575 |
| 8,706,206 B2* | 4/2014 | Kanai et al. ................... | 600/544 |
| 2005/0080344 A1 | 4/2005 | Nishii et al. | |
| 2012/0089553 A1 | 4/2012 | Mollicone et al. | |
| 2012/0133515 A1 | 5/2012 | Palshof | |
| 2012/0316845 A1 | 12/2012 | Grey et al. | |

FOREIGN PATENT DOCUMENTS

| | | | |
|---|---|---|---|
| JP | H05-342288 A | 12/1993 | |
| JP | H06-229608 A | 8/1994 | |
| JP | 2000-018670 A | 1/2000 | |
| JP | 2001-004189 A | 1/2001 | |
| JP | 2001-216363 A | 8/2001 | |

(Continued)

OTHER PUBLICATIONS

Extended European Search Report dated Nov. 18, 2014 issued in corresponding EP patent application No. 13193358.2.

(Continued)

*Primary Examiner* — Tai T Nguyen
(74) *Attorney, Agent, or Firm* — Posz Law Group, PLC

(57) ABSTRACT

A fatigue degree input unit inputs a fatigue degree of a user through use of a processing device, and writes an input value of the fatigue degree into a storage device. A recommended duration calculation unit reads the input value of the fatigue degree written by the fatigue degree input unit from the storage device. In accordance with the input value of the fatigue degree read from the storage device, the recommended duration calculation unit calculates a bath duration to be recommended to the user, as a recommended duration, through use of the processing device. A recommended duration informing unit informs the user of the recommended duration calculated by the recommended duration calculation unit, through an output device.

8 Claims, 5 Drawing Sheets

(56) References Cited

FOREIGN PATENT DOCUMENTS

| | | |
|---|---|---|
| JP | 2002-277029 A | 9/2002 |
| JP | 2005-131024 A | 5/2005 |
| JP | 2005-177128 A | 7/2005 |
| JP | 2006-317074 A | 11/2006 |
| JP | 2007-222276 A | 9/2007 |
| JP | 2011-128851 A | 6/2011 |
| JP | 2012-037222 A | 2/2012 |

OTHER PUBLICATIONS

Office Action dated Dec. 2, 2014 issued in corresponding JP patent application No. 2012-288022 (and English translation).

Search Report and Written Opinion dated Feb. 13, 2015 issued in corresponding SG patent application No. 2013084389.

* cited by examiner

LIFE MANAGEMENT APPARATUS AND LIFE MANAGEMENT METHOD

CROSS-REFERENCE TO RELATED APPLICATIONS

This application is based on and claims the benefit of priority from Japanese Patent Application No. 2012-288022, filed in Japan on Dec. 28, 2012, the content of which is incorporated herein by reference in its entirety.

TECHNICAL FIELD

The present invention relates to a life management apparatus, a life management method, and a program.

BACKGROUND ART

There is a method of controlling an indoor temperature based upon a sleeping cycle, which is a cycle with respect to the depth of sleep (for example, refer to Patent Literature 1).

There is a method of estimating a fatigue degree of a person in a room from time that has elapsed since the person started working in the room and from a detection result on the environmental conditions of the room, and controlling an indoor temperature based upon the estimated fatigue degree of the person (for example, refer to Patent Literature 2).

CITATION LIST

Patent Literature

Patent Literature 1: JP 2006-317074 A
Patent Literature 2: JP 2001-004189 A

SUMMARY OF INVENTION

Technical Problem

For leading a healthy life, it is absolutely necessary to know a physical load (fatigue) that occurs in the life (activity) of a day and take a rest (an action to recover from fatigue) in accordance with the physical load. For example, sleeping hours needed in one day may be short or long depending upon a fatigue degree of the day.

In the method described in Patent Literature 1, the indoor temperature is controlled during a person's sleeping hours. However, the duration of these sleeping hours is not based upon the consideration of the fatigue degree.

In the method described in Patent Literature 2, the action to recover from fatigue, such as sleeping, is not even taken into consideration.

An object of the present invention is, for example, to inform a user of a suitable length of time to take an action to recover from fatigue.

Solution to Problem

A life management apparatus according to one aspect of the present invention includes:

a fatigue degree input unit configured to input a fatigue degree of a user before taking an action to recover from fatigue, as a pre-action fatigue degree, and to write an input value of the pre-action fatigue degree into a storage device;

a recommended duration calculation unit configured to read the input value of the pre-action fatigue degree written by the fatigue degree input unit from the storage device, and to calculate a length of time to take the action to recover from fatigue, to be recommended to the user, as a recommended duration, in accordance with the input value of the pre-action fatigue degree read from the storage device; and a recommended duration informing unit configured to inform the user of the recommended duration calculated by the recommended duration calculation unit.

Advantageous Effects of Invention

According to one aspect of the present invention, a length of time to take an action to recover from fatigue, to be recommended to a user, is calculated in accordance with an input value of a fatigue degree of the user before taking the action to recover from fatigue, and thereby the user can be informed of a suitable length of time to take the action to recover from fatigue.

BRIEF DESCRIPTION OF DRAWINGS

The present invention will become fully understood from the detailed description given hereinafter in conjunction with the accompanying drawings, in which.

DESCRIPTION OF EMBODIMENTS

Figure 1:
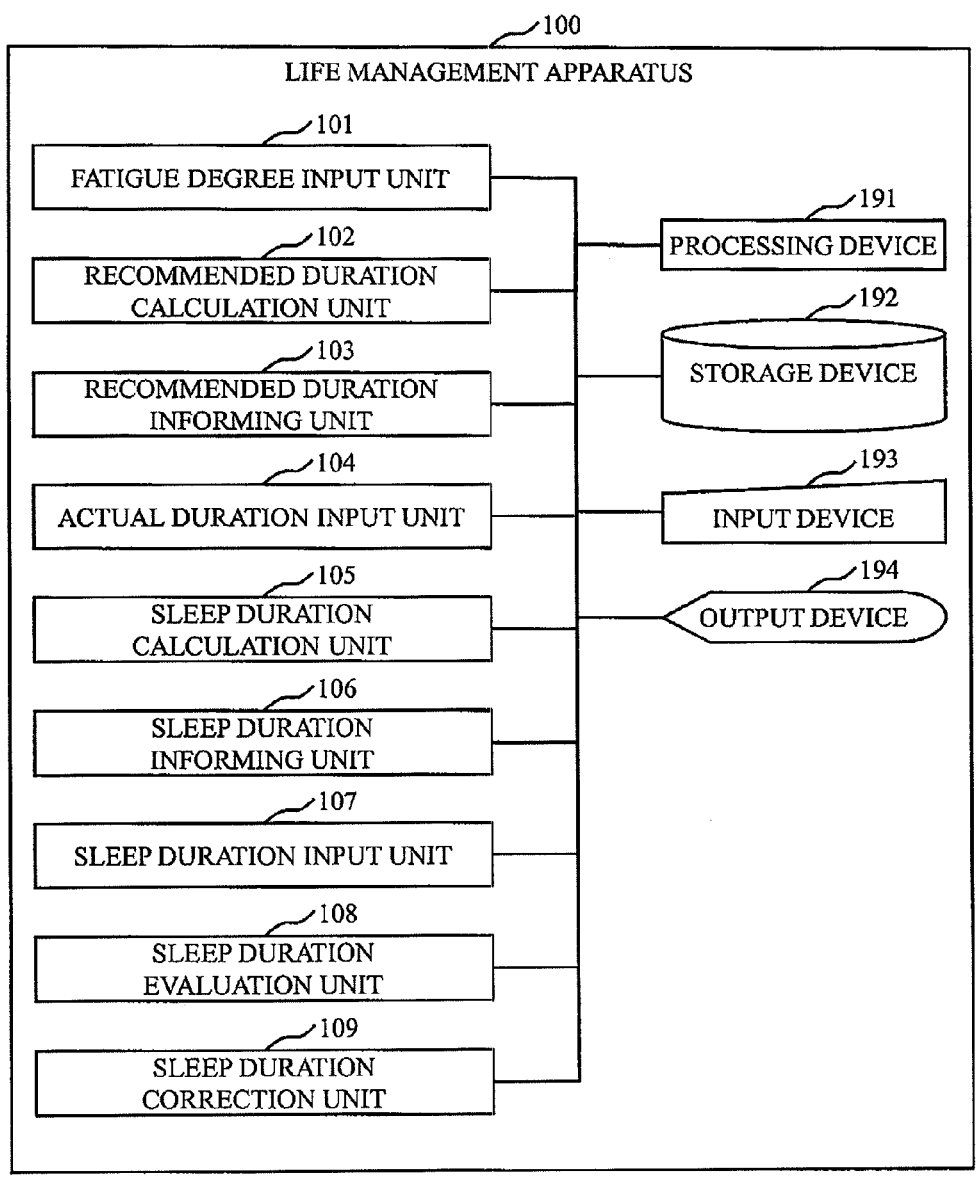
FIG. 1 is a block diagram showing a configuration of a life management apparatus according to a first embodiment.

In describing preferred embodiments illustrated in the drawings, specific terminology is employed for the sake of clarity. However, the disclosure of the present invention is not intended to be limited to the specific terminology so selected, and it is to be understood that each specific element includes all technical equivalents that operate in a similar manner and achieve a similar result.

Embodiments of the present invention will be described hereinafter with reference to the drawings.

First Embodiment

FIG. 1 is a block diagram showing a configuration of a life management apparatus 100 according to the present embodiment.

Referring to FIG. 1, the life management apparatus 100 includes a fatigue degree input unit 101, a recommended duration calculation unit 102, a recommended duration informing unit 103, an actual duration input unit 104, a sleep duration calculation unit 105, a sleep duration informing unit 106, a sleep duration input unit 107, a sleep duration evaluation unit 108, and a sleep duration correction unit 109.

The life management apparatus 100 also includes hardware, such as a processing device 191, a storage device 192, an input device 193, and an output device 194. The hardware is used by each unit of the life management apparatus 100. For example, the processing device 191 is used for computing, processing, reading, writing, etc. of data and information in each unit of the life management apparatus 100. The storage device 192 is used for storing the data and information. The input device 193 is used for inputting the data and information. The output device 194 is used for outputting the data and information.

The fatigue degree input unit 101 inputs a fatigue degree of a user before taking a bath, as a pre-action fatigue degree, through the input device 193, and writes the input value of the pre-action fatigue degree into the storage device 192.

Taking a bath (e.g., taking a shower or taking a hanshin-yoku which means "lower body bathing" in Japanese) is an example of taking an action to recover from fatigue. The present embodiment may be applied to taking a hanshinyoku alone among different ways of taking a bath, instead of all the ways of taking a bath, or may be applied to taking another action or a combination of taking multiple actions including another action.

The recommended duration calculation unit 102 reads the input value of the pre-action fatigue degree written by the fatigue degree input unit 101 from the storage device 192. Then, in accordance with the input value of the pre-action fatigue degree read from the storage device 192, the recommended duration calculation unit 102 calculates a bath duration to be recommended to the user, as a recommended duration, through use of the processing device 191.

The bath duration to be recommended to the user is the length of time to take a bath, to be recommended to the user.

The recommended duration informing unit 103 informs the user of the recommended duration calculated by the recommended duration calculation unit 102, through the output device 194.

The actual duration input unit 104 inputs an actual bath duration of the user, as an actual duration, through the input device 193.

The actual bath duration of the user is the length of time actually taken by the user to take a bath.

When the actual duration input by the actual duration input unit 104 is shorter than the recommended duration calculated by the recommended duration calculation unit 102, the sleep duration calculation unit 105 calculates a sleep duration to be recommended to the user, in accordance with the difference between the recommended duration and the actual duration, through use of the processing device 191. When calculating the sleep duration to be recommended to the user, if correction information, that is to be described later, has already been written in the storage device 192 by the sleep duration correction unit 109, the sleep duration calculation unit 105 reads the correction information written by the sleep duration correction unit 109 from the storage device 192. Using the read correction information, the sleep duration calculation unit 105 calculates (i.e., corrects) the sleep duration to be recommended to the user, through use of the processing device 191.

The sleep duration to be recommended to the user is the length of time to sleep, to be recommended to the user.

The sleep duration informing unit 106 informs the user of the sleep duration calculated by the sleep duration calculation unit 105, through the output device 194.

The sleep duration input unit 107 inputs an actual sleep duration of the user through the input device 193, The actual sleep duration of the user is the length of time actually taken by the user to sleep.

The sleep duration evaluation unit 108 evaluates the sleep duration input by the sleep duration input unit 107 against the sleep duration calculated by the sleep duration calculation unit 105, through use of the processing device 191, and informs the user of the evaluation result through the output device 194.

In addition to the pre-action fatigue degree, the fatigue degree input unit 101 inputs a fatigue degree of the user after sleeping, as a post-sleep fatigue degree, through the input device 193, and writes the input value of the post-sleep fatigue degree into the storage device 192.

The sleep duration correction unit 109 reads the input value of the post-sleep fatigue degree written by the fatigue degree input unit 101 from the storage device 192. Then, based on the input value of the post-sleep fatigue degree read from the storage device 192 and the difference between the sleep duration calculated by the sleep duration calculation unit 105 and the sleep duration input by the sleep duration input unit 107, the sleep duration correction unit 109 generates correction information for the sleep duration to be calculated by the sleep duration calculation unit 105, through use of the processing device 191, and writes the correction information into the storage device 192.

Figure 2:
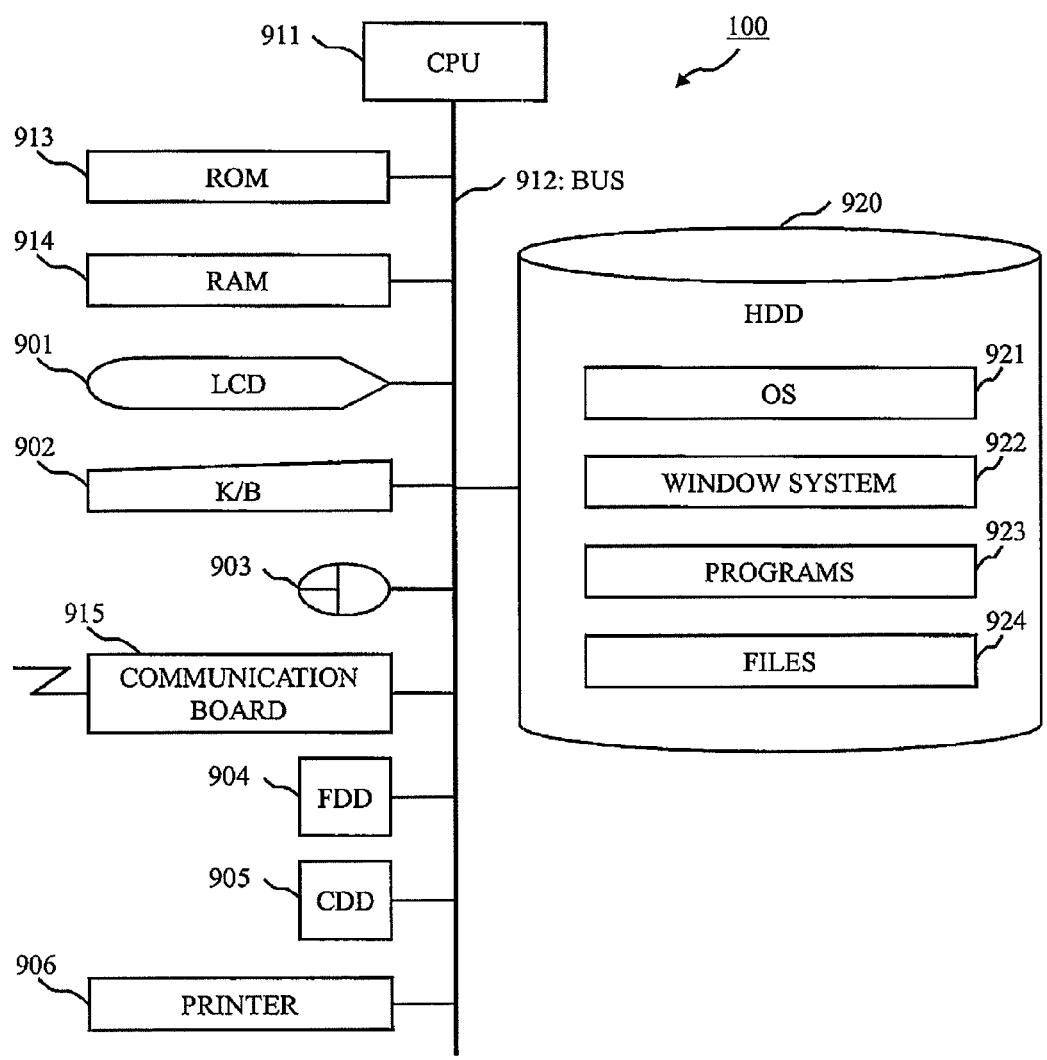
FIG. 2 shows an example of a hardware configuration of the life management apparatus according to the first embodiment.

FIG. 2 shows an example of a hardware configuration of the life management apparatus 100.

Referring to FIG. 2, the life management apparatus 100 being a computer includes hardware devices, such as an LCD (Liquid Crystal Display) 901, a keyboard (K/B) 902, a mouse 903, an FDD (Flexible Disk Drive) 904, a CDD (Compact Disc Drive) 905, and a printer 906. These hardware devices are connected to each other by cables or signal lines. A CRT (Cathode Ray Tube) or another display device may be used instead of the LCD 901. A touch panel, a touch pad, a trackball, a pen tablet, or another pointing device may be used instead of the mouse 903.

The life management apparatus 100 includes a CPU (Central Processing Unit) 911 to execute programs. The CPU 911 is an example of the processing device 191. The CPU 911 is connected via a bus 912 to a ROM (Read Only Memory) 913, a RAM (Random Access Memory) 914, a communication board 915, the LCD 901, the keyboard 902, the mouse 903, the FDD 904, the CDD 905, the printer 906, and an HDD (Hard Disk Drive) 920, and controls these hardware devices. A flash memory, an optical disc drive, a memory card reader/writer, or another storage medium may be used instead of the HDD 920.

The RAM 914 is an example of a volatile memory. The ROM 913, the FDD 904, the CDD 905, and the HDD 920 are examples of a nonvolatile memory. These are examples of the storage device 192. The communication board 915, the keyboard 902, the mouse 903, the FDD 904, and the CDD 905 are examples of the input device 193. The communication board 915, the LCD 901, and the printer 906 are examples of the output device 194.

The communication board 915 is connected to a LAN (Local Area Network) or the like. The communication board 915 may be connected not only to the LAN but also to a WAN (Wide Area Network), such as an IP-VPN (Internet Protocol Virtual Private Network), a wide area LAN and an ATM (Asynchronous Transfer Mode) network, or to the Internet. The LAN, the WAN, and the Internet are examples of a network.

The HDD 920 stores an operating system (OS) 921, a window system 922, programs 923, and files 924. Each program of the programs 923 is executed by the CPU 911, the operating system 921, and the window system 922. The programs 923 include a program to implement functions each described as " . . . unit" in the explanation of the present embodiment. The program is read and executed by the CPU 911. As items of " . . . file", " . . . database", and . . . table, the files 924 include data, information, signal values, variable values, and parameters that are described as "... data", "... information", "... ID (identifier)", "... flag", or "... result" in the explanation of the present embodiment. "... file", "... database", and "... table" are stored in a storage medium, such as the RAM 914 and the HDD 920. The data, the information, the signal values, the variable values, and the parameters stored in the storage medium, such as the RAM 914 and the HDD 920 are read into a main memory or a cache memory by the CPU 911 via a read/write circuit, and used for processing (operations) of the CPU 911, such as extraction, search, reference, comparison, computation, calculation, control, output, printing, and displaying. During the processing of the CPU 911, such as extraction, search, reference, comparison, computation, calculation, control, output, printing, and displaying, the data, the information, the signal values, the variable values, and the parameters are temporarily stored in the main memory, the cache memory, or a buffer memory.

Arrows shown in block diagrams or flowcharts used for explaining the present embodiment mainly indicate input/output of data or signals. The data or signals are stored in a memory such as the RAM 914, in a flexible disk (FD) of the FDD 904, in a compact disc (CD) of the CDD 905, in a magnetic disk of the HDD 920, in an optical disc, in a DVD (Digital Versatile Disc) or in another storage medium. Further, the data or signals are transmitted through the bus 912, the signal lines, the cables, or another transmission medium.

What is described as "... unit" in the explanation of the present embodiment may be "... circuit", "... device", or "... equipment", or may be "... step", "... process", "... procedure", or "... processing." That is, what is described as "... unit" may be implemented by firmware stored in the ROM 913. Alternatively, what is described as "... unit" may be implemented either by software alone or hardware alone, such as an element, a device, a substrate, or a wiring line. Alternatively, what is described as "... unit" may be implemented by a combination of software and hardware, or by a combination of software, hardware, and firmware. Firmware and software are stored, as programs, in the storage medium, such as the flexible disk, the compact disc, the magnetic disk, the optical disc, and the DVD. The programs are read and executed by the CPU 911. That is, the programs cause the computer to function as "... unit" described in the explanation of the present embodiment. Alternatively, the programs cause the computer to execute a procedure or a method of "... unit" described in the explanation of the present embodiment.

Figure 3:
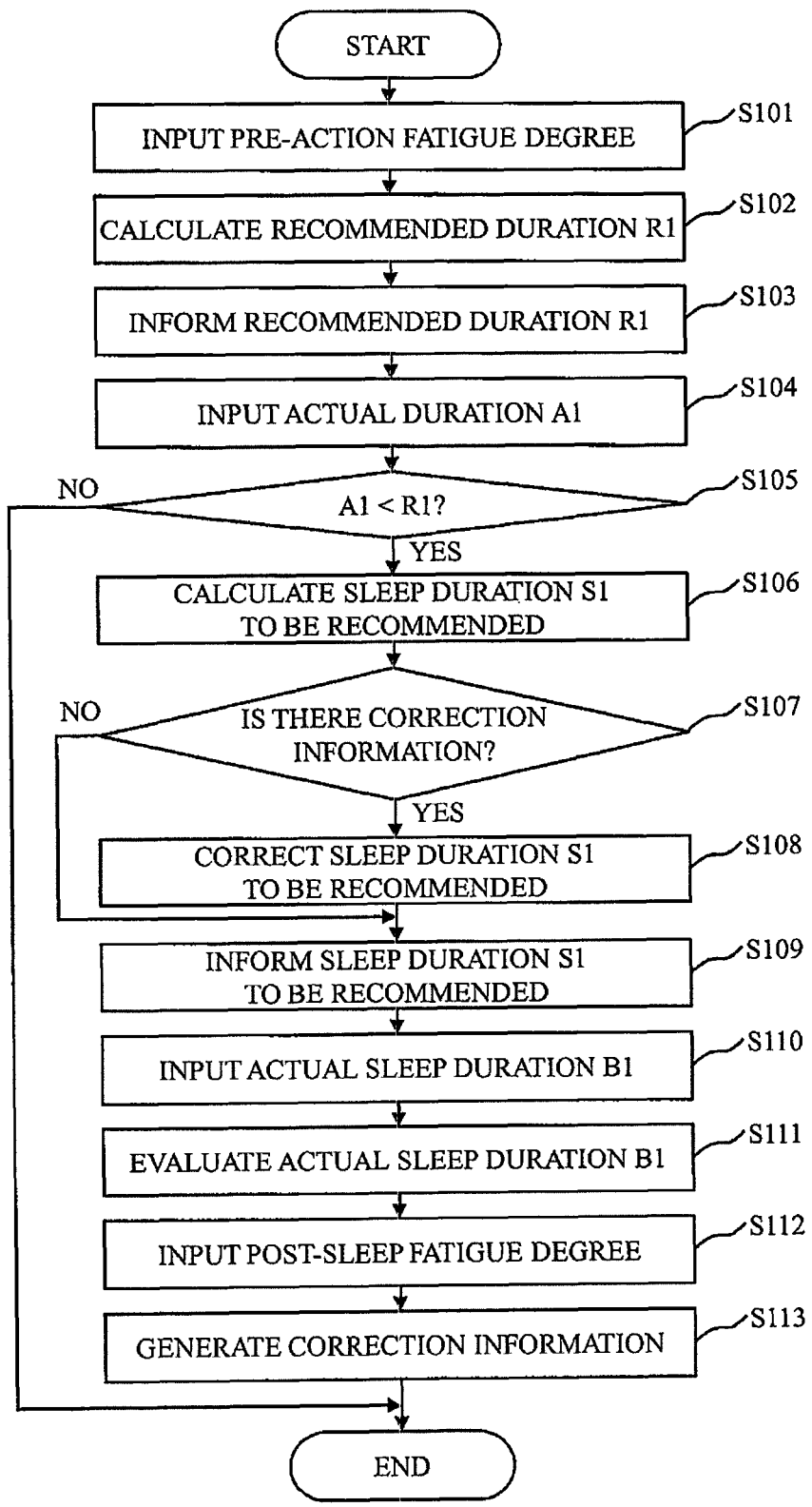
FIG. 3 is a flowchart showing an example of operations of the life management apparatus according to the first embodiment.

FIG. 3 is a flowchart showing an example of operations of the life management apparatus 100 (i.e., a life management method according to the present embodiment, or processing procedures of a program according to the present embodiment).

In the example of FIG. 3, it is assumed that the life management apparatus 100 is installed in a house of a user U1. The user U1 is an example of a user.

In Step S101, the fatigue degree input unit 101 inputs a pre-action fatigue degree of the user U1 through the input device 193 by one or more methods described below.

(1) The user U1, when returning home after going out (e.g., going to work), manually inputs a fatigue degree (e.g., a five level evaluation) of that time into a mobile terminal. When the user U1 inputs the fatigue degree, the mobile terminal transmits the input data indicating the fatigue degree to the life management apparatus 100. The fatigue degree input unit 101 receives the input data transmitted from the mobile terminal. The fatigue degree indicated by this input data is equivalent to the pre-action fatigue degree of the user U1.

(2) The user U1 goes out (e.g., goes to work) wearing shoes in which a weight sensor with a wireless communication function is embedded. When the user U1 returns home, a wireless reader installed in the front door or the like reads measured data of the day from the weight sensor, and transmits the read measured data to the life management apparatus 100. The fatigue degree input unit 101 receives the measured data transmitted from the wireless reader. Using the received measured data, the fatigue degree input unit 101 calculates the duration in which the user U1 walked on the day, the duration in which the user U1 ran on the day, and the like through use of the processing device 191. Based on the calculation result, the fatigue degree input unit 101 obtains the pre-action fatigue degree (e.g., a five level evaluation) of the user U1 by using a conversion formula defined in advance or a conversion table stored in the storage device 192 in advance. Alternatively, the fatigue degree input unit 101 accumulates measured data per day in the storage device 192, calculates a mean value of measured data per unit, such as per week, per month, and per year, and obtains the pre-action fatigue degree of the user U1 in accordance with the difference between the mean value of measured data and the measured data of the day. The pre-action fatigue degree of the user U1 is, for example, a five level evaluation being Fatigue Degree "1" or "2" if the mean value of measured data is greater than the measured data of the day, Fatigue Degree "3" if there is no difference, and Fatigue Degree "4" or "5" if the mean value of measured data is less than the measured data of the day, (3) The user U1 goes out (e.g., goes to work) wearing clothes in which a sweat sensor with a wireless communication function is embedded. When the user U1 returns home, a wireless reader installed in the front door or the like reads measured data of the day from the sweat sensor, and transmits the read measured data to the life management apparatus 100. The fatigue degree input unit 101 receives the measured data transmitted from the wireless reader. Using the received measured data, the fatigue degree input unit 101 calculates the amount of sweating and the like of the user U1 on the day through use of the processing device 191. Based on the calculation result, the fatigue degree input unit 101 obtains the pre-action fatigue degree (e.g., a five level evaluation) of the user U1 by using a conversion formula defined in advance or a conversion table stored in the storage device 192 in advance. Alternatively, similarly to the example described above, the fatigue degree input unit 101 obtains the pre-action fatigue degree of the user U1 in accordance with the difference between a mean value of measured data and the measured data of the day.

(4) The user U1 goes out (e.g., goes to work) having a pedometer with a wireless communication function or having a mobile terminal with a function equivalent to that of a pedometer. When the user U1 returns home, a wireless reader installed in the front door or the like reads measured data of the day from the pedometer, and transmits the read measured data to the life management apparatus 100. Alternatively, the mobile terminal is operated by the user U1 to transmit the same measured data to the life management apparatus 100. The fatigue degree input unit 101 receives the measured data transmitted from the wireless reader or the mobile terminal. Based on the number of steps of the user U1 on the day indicated by the received measured data, the fatigue degree input unit 101 obtains the pre-action fatigue degree (e.g., a five level evaluation) of the user U1 by using a conversion formula defined in advance or a conversion table stored in the storage device 192 in advance. Alternatively, similarly to the examples described above, the fatigue degree input unit 101 obtains the pre-action fatigue degree of the user U1 in accordance with the difference between a mean value of measured data and the measured data of the day.

(5) The user U1, when returning home after going out (e.g., pint to work), measures a blood pressure and a cardiac rate by using a blood pressure meter and a cardiac rate meter each with a wireless communication function. When the user U1 measures the blood pressure and the cardiac rate, a wireless reader installed in the house reads the measured data from the blood pressure meter and the cardiac rate meter, and transmits the read measured data to the life management apparatus 100. The fatigue degree input unit 101 receives the measured data transmitted from the wireless reader. Based on the blood pressure and the cardiac rate indicated by the received measured data, the fatigue degree input unit 101 obtains the pre-action fatigue degree (e.g., a five level evaluation) of the user U1 by using a conversion formula defined in advance or a conversion table stored in the storage device 192 in advance. Alternatively, similarly to the examples described above, the fatigue degree input unit 101 obtains the pre-action fatigue degree of the user U1 in accordance with the difference between a mean value of measured data and the measured data of when the user U1 returns home.

(6) The indoor position of the user U1 is always detected by an air conditioner with an infrared sensor or a camera, which is installed in each room of the house, and recorded as a log. At a predetermined time in the evening or night, the air conditioner transmits position data (log) of the user U1 per time on the day to the life management apparatus 100. The fatigue degree input unit 101 receives the position data transmitted from the air conditioner. Using the received position data, the fatigue degree input unit 101 calculates the amount of activity and the like of the user U1 on the day through use of the processing device 191. Based on the calculation result, the fatigue degree input unit 101 obtains the pre-action fatigue degree (e.g., a five level evaluation) of the user U1 by using a conversion formula defined in advance or a conversion table stored in the storage device 192 in advance. Alternatively, similarly to the examples described above, the fatigue degree input unit 101 obtains the pre-action fatigue degree of the user U1 in accordance with the difference between a mean value of amounts of activity of the user U1 and the amount of activity of the user U1 of the day.

(7) Various methods other than the methods (1) to (6) described above are possible. For example, even with respect to the same person, since the fatigue degree changes as the person gets older, data which the fatigue degree input unit 101 acquires by a method such as the methods (1) to (6) described above can be accumulated in a storage or a cloud on a network such as the Internet in order to be used when obtaining the pre-action fatigue degree by a method such as the methods (2) to (6) described above. The data which the fatigue degree input unit 101 acquires may not be transmitted from the mobile terminal or the wireless reader, and instead, for example, may be directly entered by the user U1 or directly transmitted from sensors.

The fatigue degree input unit 101 writes the input value of the pre-action fatigue degree obtained by one or more methods described above into the storage device 192.

In Step S102, the recommended duration calculation unit 102 reads the input value of the pre-action fatigue degree written in Step S101, from the storage device 192. Then, from the input value of the pre-action fatigue degree read from the storage device 192, the recommended duration calculation unit 102 calculates a bath duration to be recommended to the user U1, as a recommended duration R1, by using a conversion formula defined in advance or a conversion table stored in the storage device 192 in advance, through use of the processing device 191.

In Step S103, the recommended duration informing unit 103 informs the user U1 of the recommended duration R1 calculated in Step S102, by displaying it on screen through the output device 194. Thereby, the user U1 is able to know a suitable bath duration of the day.

In Step S104, the actual duration input unit 104 inputs an actual bath duration of the user U1, as an actual duration A1, through the input device 193 by one or more methods described below.

(1) A flow amount sensor to measure the amount of hot water supplied to the bathtub from a hot water storage tank of a hot water supply system is installed in at least one position of the hot water storage tank. The actual duration input unit 104 receives measured data of the amount of hot water directly from the flow amount sensor or indirectly through communication equipment such as a wireless reader. Using the received measured data, the actual duration input unit 104 determines whether the user U1 is taking a bath and measures the duration in which the user U1 is taking a bath.

(2) The actual duration input unit 104 receives information indicating the open/closed state of a bathroom door directly from an open/closed sensor installed in the bathroom door or indirectly through communication equipment such as a wireless reader. Based on the received information, the actual duration input unit 104 determines whether the user U1 is taking a bath and measures the duration in which the user U1 is taking a bath.

(3) The actual duration input unit 104 receives information indicating the on/off state of lighting directly from a lighting device in the bathroom or indirectly through communication equipment such as a wireless reader. Based on the received information, the actual duration input unit 104 determines whether the user U1 is taking a bath and measures the duration in which the user U1 is taking a bath.

(4) The actual duration input unit 104 receives an input of the bath duration from the user U1 through a touch panel or the like.

(5) Various methods other than the methods (1) to (4) described above are possible.

In Step S105, the sleep duration calculation unit 105 compares the recommended duration R1 calculated in Step S102 with the actual duration A1 input in Step S104, through use of the processing device 191. In the case where the actual duration A1 is shorter than the recommended duration R1, Step S106 follows. In the case where the actual duration A1 is not shorter than the recommended duration R1, the processing ends.

In Step S106, from the difference between the recommended duration R1 calculated in Step S102 and the actual duration A1 input in Step S104, the sleep duration calculation unit 105 calculates a sleep duration S1 to be recommended to the user U1 by using a conversion formula defined in advance or a conversion table stored in the storage device 192 in advance, through use of the processing device 191.

In Step S107, the sleep duration calculation unit 105 determines, through use of the processing device 191, whether correction information has already been written in the storage device 192 by the sleep duration correction unit 109. If correction information has been written, Step S108 follows. If correction information has not been written, Step S109 follows.

In Step S108, the sleep duration calculation unit 105 reads the correction information written in Step S113 to be described later (e.g., Step S113 in the processing performed on the previous day) from the storage device 192. Using the read correction information, the sleep duration calculation unit 105 corrects the sleep duration S1 calculated in Step S106, through use of the processing device 191.

In Step S109, the sleep duration informing unit 106 informs the user U1 of the sleep duration S1 calculated in Step S106 (or, if corrected in Step S108, the corrected sleep duration S1), by displaying it on screen through the output device 194. Thereby, the user U1 is able to know a suitable sleep duration of the day.

In Step S110, the sleep duration input unit 107 inputs an actual steep duration B1 of the user U1 through the input device 193 by one or more methods described below.

(1) The sleep duration input unit 107 receives information indicating whether the weight of the user U1 is detected or not, directly from a weight sensor installed in the bed in the bedroom or indirectly through communication equipment such as a wireless reader. Based on the received information, the sleep duration input unit 107 determines whether the user U1 is sleeping and measures the sleep duration B1 of the user U1.

(2) The sleep duration input unit 107 receives an input of the sleep duration B1 from the user U1 through a touch panel or the like.

(3) Various methods other than the methods (1) and (2) described above are possible.

In Step S111, the sleep duration evaluation unit 108 evaluates the sleep duration B1 input in Step S110 against the sleep duration S1 calculated in Step S106 (or, if corrected in Step S108, the corrected sleep duration S1), by giving a score, through use of the processing device 191. The sleep duration evaluation unit 108 informs the user U1 of the score by displaying it on screen through the output device 194. Thereby, the user U1 is able to obtain a sleep duration index.

In Step S112, the fatigue degree input unit 101 inputs a post-sleep fatigue degree of the user U1 through the input device 193 by one or more methods described below.

(1) The user U1, when waking up from sleep (when getting out of bed), manually inputs a fatigue degree (e.g., a five level evaluation) of that time into a mobile terminal. When the user U1 inputs the fatigue degree, the mobile terminal transmits the input data indicating the fatigue degree to the life management apparatus 100. The fatigue degree input unit 101 receives the input data transmitted from the mobile terminal. The fatigue degree indicated by this input data is equivalent to the post-sleep fatigue degree of the user U1.

(2) The user U1, when waking up from sleep (when getting out of bed), measures a blood pressure and a cardiac rate by using a blood pressure meter and a cardiac rate meter each with a wireless communication function. When the user U1 measures the blood pressure and the cardiac rate, a wireless reader installed in the house reads the measured data from the blood pressure meter and the cardiac rate meter, and transmits the read measured data to the life management apparatus 100. The fatigue degree input unit 101 receives the measured data transmitted from the wireless reader. Based on the blood pressure and the cardiac rate indicated by the received measured data, the fatigue degree input unit 101 obtains the post-sleep fatigue degree (e.g., a five level evaluation) of the user U1 by using a conversion formula defined in advance or a conversion table stored in the storage device 192 in advance. Alternatively, the fatigue degree input unit 101 accumulates measured data per day and time in the storage device 192, calculates a mean value of measured data per unit, such as per day, per week, per month, and per year, and obtains the post-sleep fatigue degree of the user U1 in accordance with the difference between the mean value of measured data and the measured data of when the user U1 gets out of bed.

(3) Various methods other than the methods (1) and (2) described above are possible. For example, even with respect to the same person, since the fatigue degree changes as the person gets older, data which the fatigue degree input unit 101 acquires by a method such as the methods (1) and (2) described above can be accumulated in a storage or a cloud on a network such as the Internet in order to be used when obtaining the post sleep fatigue degree by a method such as the method (2) described above. The data which the fatigue degree input unit 101 acquires may not be transmitted from the mobile terminal or the wireless reader, and instead, for example, may be directly entered by the user U1 or directly transmitted from sensors.

The fatigue degree input unit 101 writes the input value of the post-sleep fatigue degree obtained by one or more methods described above into the storage device 192.

In Step S113, the sleep duration correction unit 109 reads the input value of the post-sleep fatigue degree written in Step S112, from the storage device 192. Then, if the input value of the post-sleep fatigue degree read from the storage device 192 is the lower limit of the post-sleep fatigue degree (i.e., if the user U1 has completely recovered from fatigue), the processing ends. If the input value of the post-sleep fatigue degree read from the storage device 192 is not the lower limit of the post-sleep fatigue degree (i.e., if the user U1 still remains fatigued), the sleep duration correction unit 109 generates, through use of the processing device 191, correction information (e.g., a correction coefficient used in the conversion formula described above or a correction value applied to the conversion table described above) for the sleep duration S1 to be calculated in Step S106 (e.g., Step S106 in the processing to be performed on the following day), based on the input value of the post-sleep fatigue degree and the difference between the sleep duration S1 calculated in Step S1106 (or, if corrected in Step S108, the corrected sleep duration S1) and the sleep duration B1 input in Step S110, and writes the correction information into the storage device 192. Then, the processing ends.

Second Embodiment

With respect to a second embodiment, the difference from the first embodiment will be mainly described.

Figure 4:
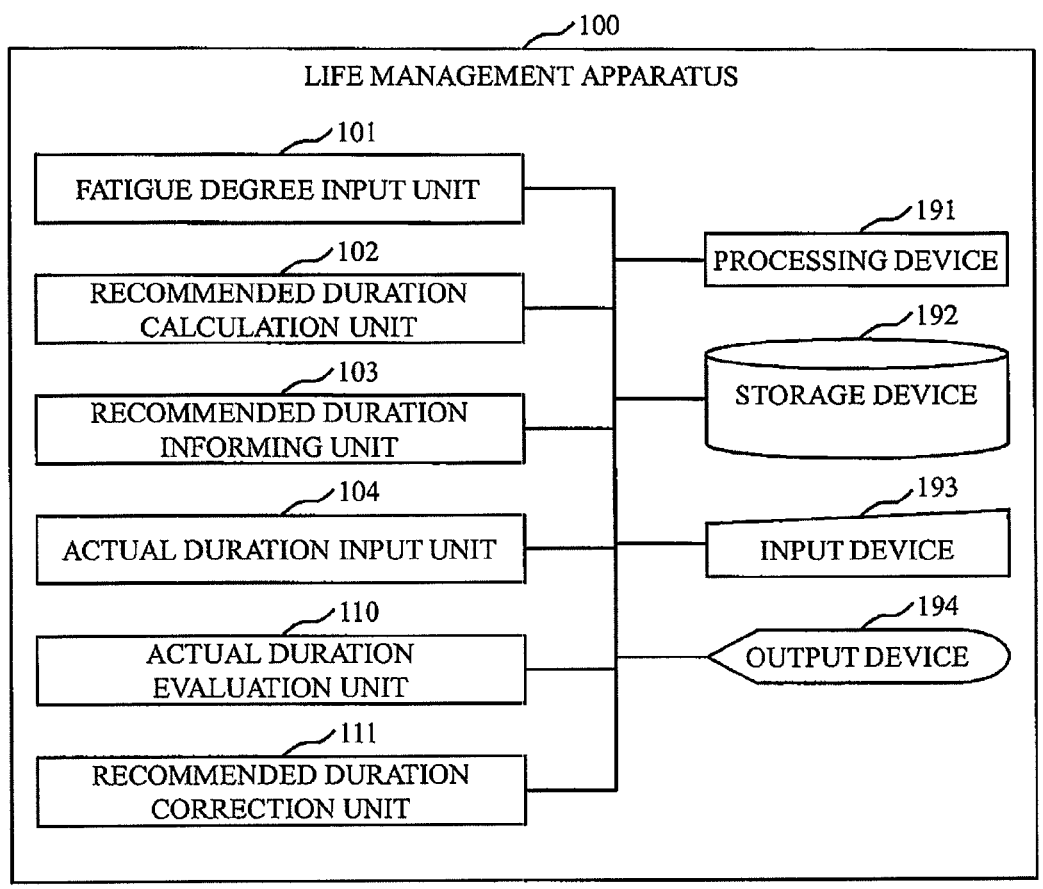
FIG. 4 is a block diagram showing a configuration of a life management apparatus according to a second embodiment.

FIG. 4 is a block diagram showing a configuration of a life management apparatus 100 according to the present embodiment.

Referring to FIG. 4, the life management apparatus 100 includes the fatigue degree input unit 101, the recommended duration calculation unit 102, the recommended duration informing unit 103 and the actual duration input unit 104 as in the first embodiment, and further includes an actual duration evaluation unit 110 and a recommended duration correction unit 111.

The fatigue degree input unit 101 inputs a fatigue degree of a user before sleeping, as a pre-action fatigue degree, through the input device 193, and writes the input value of the pre-action fatigue degree into the storage device 192.

In the present embodiment, sleeping is an example of taking an action to recover from fatigue. The present embodiment may be applied to taking a bath, as in the first embodiment, instead of sleeping, may be applied to taking a hanshinyoku alone among different ways of taking a bath, may be applied to a combination of taking a bath and sleeping, or may be applied to taking another action or a combination of taking multiple actions including another action.

The recommended duration calculation unit 102 reads the input value of the pre-action fatigue degree written by the fatigue degree input unit 101 from the storage device 192. Then, in accordance with the input value of the pre-action fatigue degree read from the storage device 192, the recommended duration calculation unit 102 calculates a sleep duration to be recommended to the user, as a recommended duration, through use of the processing device 191. When calculating the recommended duration, if correction information, that is to be described later, has already been written in the storage device 192 by the recommended duration correction unit 111, the recommended duration calculation unit 102 reads the correction information written by the recommended duration correction unit 111 from the storage device 192. Using the read correction information, the recommended duration calculation unit 102 calculates (i.e., corrects) the recommended duration through use of the processing device 191.

As in the first embodiment, the recommended duration informing unit 103 informs the user of the recommended duration calculated by the recommended duration calculation unit 102, through the output device 194.

The actual duration input unit 104 inputs an actual sleep duration of the user, as an actual duration, through the input device 193.

The actual duration evaluation unit 110 evaluates the actual duration input by the actual duration input unit 104 against the recommended duration calculated by the recommended duration calculation unit 102, through use of the processing device 191, and informs the user of the evaluation result through the output device 194.

In addition to the pre-action fatigue degree, the fatigue degree input unit 101 inputs a fatigue degree of the user after sleeping, as a post-action fatigue degree, through the input device 193, and writes the input value of the post-action fatigue degree into the storage device 192.

The recommended duration correction unit 111 reads the input value of the post-action fatigue degree written by the fatigue degree input unit 101 from the storage device 192. Then, based on the input value of the post-action fatigue degree read from the storage device 192 and the difference between the recommended duration calculated by the recommended duration calculation unit 102 and the actual duration input by the actual duration input unit 104, the recommended duration correction unit 111 generates correction information for the recommended duration to be calculated by the recommended duration calculation unit 102, through use of the processing device 191, and writes the correction information into the storage device 192.

Figure 5:
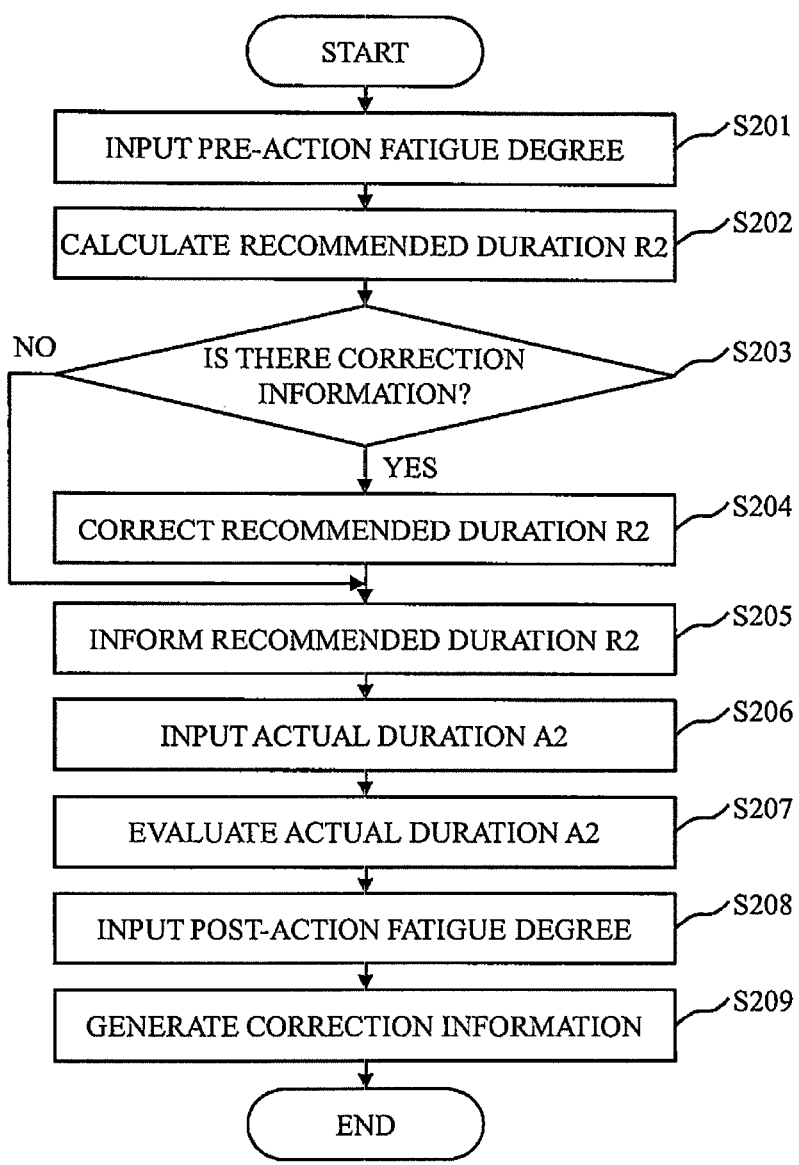
FIG. 5 is a flowchart showing an example of operations of the life management apparatus according to the second embodiment.

FIG. 5 is a flowchart showing an example of operations of the life management apparatus 100 (i.e., a life management method according to the present embodiment, or processing procedures of a program according to the present embodiment).

In the example of FIG. 5, it is assumed that the life management apparatus 100 is installed in a house of a user U2. The user U2 is an example of a user.

In Step S201, the fatigue degree input unit 101 inputs a pre-action fatigue degree of the user U2 through the input device 193 by the same methods as those of Step S101 of FIG. 3, and writes the input value of the pre-action fatigue degree into the storage device 192.

In Step S202, the recommended duration calculation unit 102 reads the input value of the pre-action fatigue degree written in Step S201, from the storage device 192. Then, from the input value of the pre-action fatigue degree read from the storage device 192, the recommended duration calculation unit 102 calculates a sleep duration to be recommended to the user U2, as a recommended duration R2, by using a conversion formula defined in advance or a conversion table stored in the storage device 192 in advance, through use of the processing device 191. Alternatively, the recommended duration calculation unit 102 accumulates data indicating a sleep duration per day, a pre-action fatigue degree per day, and a post-action fatigue degree per day in the storage device 192, analyzes a correlation between a sleep duration and a fatigue recovery degree (i.e., the difference between a pre-action fatigue degree and a post-action fatigue degree), per unit, such as per week, per month, and per year, and then, based on the analysis result, obtains a sleep duration suitable for the pre-action fatigue degree of the user U2 of the day (i.e., a sleep duration which enables the user U2 to recover from fatigue).

In Step S203, the recommended duration calculation unit 102 determines, through use of the processing device 191, whether correction information has already been written in the storage device 192 by the recommended duration correction unit 111. If correction information has been written, Step S204 follows. If correction information has not been written, Step S205 follows.

In Step S204, the recommended duration calculation unit 102 reads the correction information written in Step S209 to be described later (e.g., Step S209 in the processing performed on the previous clay) from the storage device 192. Using the read correction information, the recommended duration calculation unit 102 corrects the recommended duration R2 calculated in Step S202, through use of the processing device 191.

In Step S205, the recommended duration informing unit 103 informs the user U2 of the recommended duration R2 calculated in Step S202 (or, if corrected in Step S204, the corrected recommended duration R2), by displaying it on screen through the output device 194. Thereby, the user U2 is able to know a suitable sleep duration of the day.

In Step S206, the actual duration input unit 104 inputs an actual sleep duration of the user U2, as an actual duration A2, through the input device 193 by the same methods as those of Step S110 of FIG. 3.

In Step S207, the actual duration evaluation unit 110 evaluates the actual duration A2 input in Step S206 against the recommended duration R2 calculated in Step S202 (or, if corrected in Step S204, the corrected recommended duration R2), by giving a score, through use of the processing device 191. The actual duration evaluation unit 110 informs the user U2 of the score by displaying it on screen through the output device 194. Thereby, the user U2 is able to obtain a sleep duration index.

In Step S208, the fatigue degree input unit 101 inputs a post-action fatigue degree of the user U2 through the input device 193 by the same methods as those of Step S112 of FIG. 3, and writes the input value of the post-action fatigue degree into the storage device 192.

In Step S209, the recommended duration correction unit 111 reads the input value of the post-action fatigue degree written in Step S208, from the storage device 192. Then, if the input value of the post-action fatigue degree read from the storage device 192 is the lower limit of the post-action fatigue degree (i.e., if the user U2 has completely recovered from fatigue), the processing ends. If the input value of the post-action fatigue degree read from the storage device 192 is not the lower limit of the post-action fatigue degree (i.e., if the user U2 still remains fatigued), the recommended duration correction unit 111 generates, through use of the processing device 191, correction information (e.g., a correction coefficient used in the conversion formula described above or a correction value applied to the conversion table described above) for the recommended duration R2 to be calculated in Step S202 (e.g., Step S202 in the processing to be performed on the following day), based on the input value of the post-action fatigue degree and the difference between the recommended duration R2 calculated in Step S202 (or, if corrected in Step S204, the corrected recommended duration R2) and the actual duration A2 input in Step S206, and writes the correction information into the storage device 192. Then, the processing ends.

While embodiments of the present invention have been explained above, two or more of these embodiments may be combined to be implemented. Alternatively, one of these embodiments may be partially implemented, or two or more of them may be partially combined to be implemented. The present invention is not limited to these embodiments, and various modification can be made as needed.

Numerous additional modifications and variations are possible in light of the above teachings. It is therefore to be understood that, within the scope of the appended claims, the disclosure of this patent specification may be practiced otherwise than as specifically described herein.

REFERENCE SIGNS LIST

100: life management apparatus
101: fatigue degree input unit
102: recommended duration calculation unit
103: recommended duration informing unit
104: actual duration input unit
105: sleep duration calculation unit
106: sleep duration informing unit
107: sleep duration input unit
108: sleep duration evaluation unit
109: sleep duration correction unit
110: actual duration evaluation unit
111: recommended duration correction unit
191: processing device
192: storage device
193: input device
194: output device
901: LCD
902: keyboard
903: mouse
904: FDD
905: CDD
906: printer
911: CPU
912: bus
913: ROM
914: RAM
915: communication board
920: HDD
921: operating system
922: window system
923: programs
924: files

The invention claimed is:

1. A life management apparatus comprising:
a fatigue degree input unit configured to input a fatigue degree of a user before taking an action to recover from fatigue, as a pre-action fatigue degree, and to write an input value of the pre-action fatigue degree into a storage device;
a recommended duration calculation unit configured to read the input value of the pre-action fatigue degree written by the fatigue degree input unit from the storage device, and to calculate a length of time to take the action to recover from fatigue as a recommended duration in accordance with the input value of the pre-action fatigue degree read from the storage device;
a recommended duration informing unit configured to inform the user of the recommended duration calculated by the recommended duration calculation unit;
an actual duration input unit configured to input a length of time actually taken by the user to take the action to recover from fatigue, as an actual duration;
a sleep duration calculation unit configured to calculate a sleep duration in accordance with a difference between the recommended duration calculated by the recommended duration calculation unit and the actual duration input by the actual duration input unit, when the actual duration is shorter than the recommended duration; and
a sleep duration informing unit configured to inform the user of the sleep duration calculated by the sleep duration calculation unit.

2. The life management apparatus according to claim 1, further comprising:
a sleep duration input unit configured to input an actual sleep duration of the user; and
a sleep duration evaluation unit configured to evaluate the sleep duration input by the sleep duration input unit against the sleep duration calculated by the sleep duration calculation unit, and to inform the user of an evaluation result.

3. The life management apparatus according to claim 1, wherein the fatigue degree input unit inputs a fatigue degree of the user after sleeping, as a post-sleep fatigue degree, and writes an input value of the post-sleep fatigue degree into the storage device,
the life management apparatus further comprising:
a sleep duration input unit configured to input an actual sleep duration actually taken by the user: and
a sleep duration correction unit configured to read the input value of the post-sleep fatigue degree written by the fatigue degree input unit from the storage device, to generate correction information for the sleep duration to be calculated by the sleep duration calculation unit, based on the input value of the post-sleep fatigue degree read from the storage device and a difference between the sleep duration calculated by the sleep duration calculation unit and the sleep duration input by the sleep duration input unit, and to write the correction information into the storage device,
wherein, when calculating the sleep duration to be recommended to the user, the sleep duration calculation unit reads the correction information written by the sleep duration correction unit from the storage device, and uses the read correction information.

4. The life management apparatus according to claim 1, wherein the recommended duration calculation unit calculates a bath duration to be recommended to the user, as the recommended duration.

5. The life management apparatus according to claim 1, wherein the recommended duration calculation unit calculates a sleep duration to be recommended to the user, as the recommended duration.

6. The life management apparatus according to claim 1, further comprising:
an actual duration evaluation unit configured to evaluate the actual duration input by the actual duration input unit against the recommended duration calculated by the recommended duration calculation unit, and to inform the user of an evaluation result.

7. The life management apparatus according to claim 1, wherein the fatigue degree input unit inputs a fatigue degree of the user after taking the action to recover from fatigue, as a post-action fatigue degree, and writes an input value of the post-action fatigue degree into the storage device,
the life management apparatus farther comprising:
a recommended duration correction unit configured to read the input value of the post-action fatigue degree written by the fatigue degree input unit from the storage device, to generate correction information for the recommended duration to be calculated by the recommended duration calculation unit based on the input value of the post-action fatigue degree read from the storage device and a difference between the recommended duration calculated by the recommended duration calculation unit and the actual duration input by the actual duration input unit, and to write the correction information into the storage device,
wherein, when calculating the recommended duration, the recommended duration calculation unit reads the correction information written by the recommended duration correction unit from the storage device, and uses the read correction information.

8. A life management method comprising:
inputting a fatigue degree of a user before taking an action to recover from fatigue, as a pre-action fatigue degree, and writing an input value of the pre-action fatigue degree into a storage device, by a fatigue degree input unit;
reading the input value of the pre-action fatigue degree written by the fatigue degree input unit from the storage device, and calculating a length of time to take the action to recover from fatigue as a recommended duration in accordance with the input value of the pre-action fatigue degree read from the storage device, by a recommended duration calculation unit;
informing the user of the recommended duration calculated by the recommended duration calculation unit, by a recommended duration informing unit;
inputting a length of time actually taken by the user to take the action to recover from fatigue, as an actual duration, by an actual duration input unit;
calculating a sleep duration in accordance with a difference between the recommended duration calculated by the recommended duration calculation unit and the actual duration input by the actual duration input unit, when the actual duration is shorter than the recommended duration, by a sleep duration calculation unit; and
informing the user of the sleep duration calculated by the sleep duration calculation unit by a sleep duration informing unit.

* * * * *